United States Patent [19]
Hagen et al.

[11] Patent Number: 5,886,187
[45] Date of Patent: Mar. 23, 1999

[54] BENZENE DERIVATIVES HAVING A HETEROCYCLIC RADICAL

[75] Inventors: Helmut Hagen, Frankenthal; Manfred Patsch, Wachenheim; Bernd-Peter Walther, Schwetzingen; Andrea Zamponi, Heidelberg, all of Germany

[73] Assignee: BASF Aktiengesellschaft, Ludwigshafen, Germany

[21] Appl. No.: 983,325

[22] PCT Filed: Jul. 22, 1996

[86] PCT No.: PCT/EP96/03224

§ 371 Date: Jan. 26, 1998

§ 102(e) Date: Jan. 26, 1998

[87] PCT Pub. No.: WO97/05124

PCT Pub. Date: Feb. 13, 1997

[30] Foreign Application Priority Data

Aug. 1, 1995 [DE] Germany ............................ 19528189.6

[51] Int. Cl.[6] .................... C07D 271/06; C07D 271/107; C07D 285/08; C07D 285/12

[52] U.S. Cl. .......................... 548/128; 548/131; 548/136; 548/143

[58] Field of Search .................... 548/128, 131, 548/143, 136

[56] References Cited

FOREIGN PATENT DOCUMENTS

| A 0 037 465 | 10/1981 | European Pat. Off. . |
|---|---|---|
| 0 639 562 A1 | 8/1994 | European Pat. Off. . |
| A 20 09 421 | 9/1971 | Germany . |
| 1465895 | 3/1977 | United Kingdom . |

OTHER PUBLICATIONS

I. A. Mazur et al; Synthesis of 2,3–Dihydro and 2,3,5,6,–Tetrahydro Derivatives of Imidazo [2, 1–b] Thiazole, Chemical Abstracts, vol. 72, No.3, 19 Jan. 1970, p. 334.

*Primary Examiner*—Johann Richter
*Assistant Examiner*—Jane C. Oswecki
*Attorney, Agent, or Firm*—Oblon, Spivak, McClelland, Maier & Neustadt, P.C.

[57] ABSTRACT

Benzene derivatives of the formula

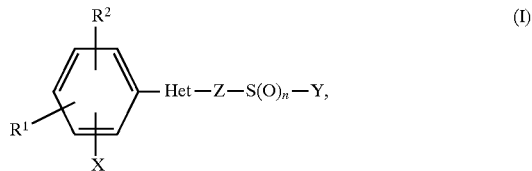

where n is 0, 1 or 2, x is nitro or amino,

Z is a direct bond or unsubstituted or substituted $C_1$–$C_6$-alkylene,

Y is vinyl or a radical of the formula $C_2H_4$—Q, where Q is hydroxyl or a group which can be removed under alkaline reaction conditions, $R^1$ and $R^2$ are hydrogen, $C_1$–$C_4$-alkyl, $C_1$–$C_4$-alkoxy, halogen, nitro, amino, hydroxysulfonyl or a radical of the formula Z—S(O)$_n$—Y, where n, Z and Y have the abovementioned meanings, and Het is the radical of a heterocyclic ring, are described.

9 Claims, No Drawings

BENZENE DERIVATIVES HAVING A HETEROCYCLIC RADICAL

This application is a 371 of PCT/EP96/03224 filed Jul. 22, 1996.

The present invention relates to novel benzene derivatives of the formula I

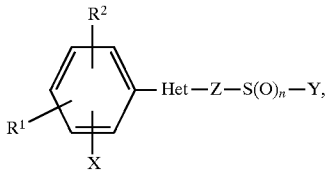

where n is 0, 1 or 2, x is nitro or amino,

Z is a direct bond or $C_1$–$C_6$-alkylene which can be interrupted by 1 or 2 oxygen or sulfur atoms in ether form or 1 or 2 nonadjacent amino, $C_1$–$C_4$-alkylamino or $C_1$–$C_4$-alkanoylimino groups, Y is vinyl or a radical of the formula $C_2H_4$—Q, where Q is hydroxyl or a group which can be removed under alkaline reaction conditions, $R^1$ and $R^2$ independently of one another are each hydrogen, $C_1$–$C_4$-alkyl, $C_1$–$C_4$-alkoxy, halogen, nitro, amino, hydroxysulfonyl or a radical of the formula Z—S(O)$_n$—Y, where n, Z and Y each have the abovementioned meanings, and Het is the radical of a 5- or 6-membered aromatic heterocyclic ring, which has 1 to 3 heteroatoms selected from the group consisting of oxygen, sulfur and nitrogen.

It is an object of the present invention to provide novel benzene derivatives having a heterocyclic radical, and which furthermore have a thioether, sulfoxide or sulfonyl group. The novel benzene derivatives should advantageously be suitable for the production of dyes.

We have found that this object is achieved by the benzene derivatives of the formula I described in greater detail at the outset.

All alkyl and alkylene groups occurring in the abovementioned formula can be either straight-chain or branched.

Radicals $R^1$ and $R^2$ are, for example, methyl, ethyl, propyl, isopropyl, butyl, isobutyl, sec-butyl, tert-butyl, methoxy, ethoxy, propoxy, isopropoxy, butoxy, isobutoxy, sec-butoxy, tert-butoxy, fluorine, chlorine or bromine.

Radicals Z are, for example, $CH_2$, $(CH_2)_2$, $(CH_2)_3$, $(CH_2)_4$, $(CH_2)_5$, $(CH_2)_6$, $CH(CH_3)CH_2$, $CH(CH_3)CH(CH_3)$, $(CH_2)_2O(CH_2)_2$, $(CH_2)_2$, $(CH_2)_2O(CH_2)_2O(CH_2)_2$, $(CH_2)_2S$ $(CH_2)_2$, $(CH_2)_3S(CH_2)_2$, $(CH_2)_2S(CH_2)_2S(CH_2)_2$, $(CH_2)_2NH$ $(CH_2)_2$, $(CH_2)_3NH(CH_2)_2$, $(CH_2)_2NH(CH_2)_2NH$ $(CH_2)_2$,

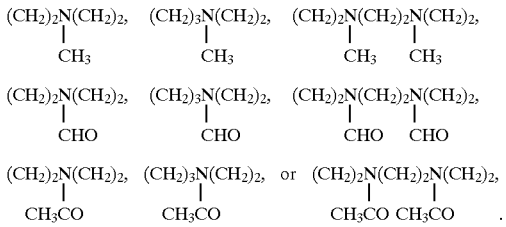

The radical Q is hydroxyl or a group which can be removed under alkaline reaction conditions. Such groups are, for example, chlorine, bromine, $C_1$–$C_4$-alkylsulfonyl, phenylsulfonyl, $OSO_3H$, $SSO_3H$, $OP(O)$ $(OH)_2$, $C_1$–$C_4$-alkylsulfonyloxy, phenylsulfonyloxy, $C_1$–$C_4$-alkanoyloxy, $C_1$–$C_4$-dialkylamino or a radical of the formula

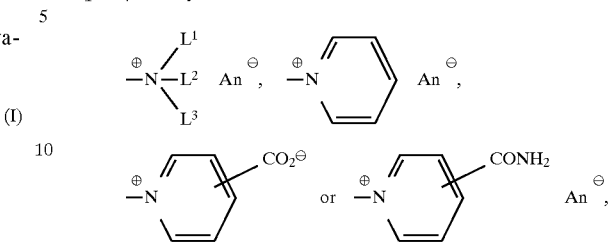

where $L^1$, $L^2$ and $L^3$ independently of one another in each case have the meaning of $C_1$–$C_4$-alkyl or benzyl and An⊖ in each case has the meaning of one equivalent of an anion. Suitable anions here are, for example, fluoride, chloride, bromide, iodide, mono-, di- or trichloroacetate, methanesulfonate, benzenesulfonate or 2- or 4-methylbenzenesulfonate.

Het is the radical of a 5- or 6-membered aromatic heterocyclic ring which has 1 to 3 heteroatoms selected from the group consisting of oxygen, sulfur and nitrogen.

Suitable heterocyclic parent structures, which can carry substituents, from which the radicals Het are derived are, for example, pyrrole, furan, thiophene, pyrazole, imidazole, oxazole, thiazole, isothiazole, 1,2,4-triazole, 1,2,4-oxadiazole, 1,3,4-oxadiazole, 1,2,4-thiadiazole, 1,3,4-thiadiazole, pyridine, pyridazine, pyrimidine or pyrazine.

Suitable substituents for the heterocyclic parent structures are, for example, $C_1$–$C_4$-alkyl, phenyl, halogen, cyano, carboxyl or $C_1$–$C_4$-alkoxycarbonyl.

To be emphasized here are 5-membered heterocycles, in particular those which have 3 heteroatoms. Particularly to be mentioned are 1,2,4-oxadiazole, 1,3,4-oxadiazole, 1,2,4-thiadiazole or 1,3,4-thiadiazole.

Preferred benzene derivatives of the formula I are those in which is 0 or 2.

Furthermore preferred benzene derivatives of the formula I are those in which Z is $C_1$–$C_4$-alkylene which can be interrupted by an oxygen atom in ether form.

Furthermore preferred benzene derivatives of the formula I are those in which Y is 2-hydroxyethyl.

Furthermore preferred benzene derivatives of the formula I are those in which $R^1$ has the abovementioned meaning and $R^2$ is hydrogen.

Furthermore preferred benzene derivatives of the formula I are those in which Het is 1,2,4-oxadiazole-3,5-diyl.

Particularly preferred benzene derivatives of the formula I are those in which $R^1$ is hydrogen, nitro, amino, hydroxysulfonyl or a radical of the formula $S(O)_nC_2H_4OH$, where n is 0 or 2, and $R^2$ is hydrogen.

Additionally preferred compounds of the formula I are those in which the substituents are selected from a combination of the preferred substituents listed above.

Of particular industrial interest are benzene derivatives of the formula Ia or Ib

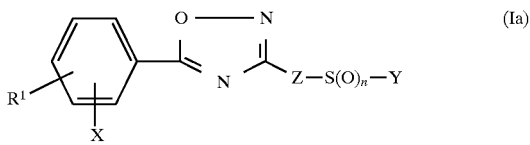

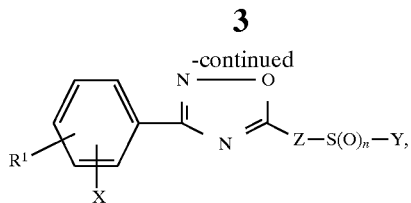

where n is 0 or 2,

X is nitro or amino,

Z is $C_1$–$C_4$-alkylene and $R^1$ is hydrogen, nitro, amino, hydroxysulfonyl or a radical of the formula $S(O)_n C_2 H_4 OH$, where n is 0 or 2, and Y has the abovementioned meanings, where 2-hydroxyethyl is particularly to be mentioned.

The novel benzene derivatives of the formula I can be prepared in ways known per se. For example, it is possible here to start from those intermediates which are suitable for synthesizing the heterocycle on which the radical Het is based.

This is explained in greater detail in the following for the case where Het is derived from 1,2,4-oxadiazole.

For example, a nitrile of the formula II

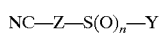

where n, Y and Z in each case have the abovementioned meanings, can be reacted with hydroxylamine and the resulting amide oxime of the formula III

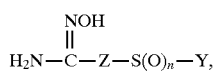

where n, Y and Z in each case have the abovementioned meanings, can be reacted with an isatoic anhydride of the formula IV

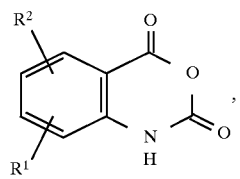

where $R^1$ and $R^2$ in each case have the abovementioned meanings. It is thus possible to obtain benzene derivatives of the formula Ic

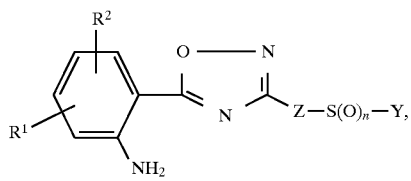

where n, $R^1$, $R^2$, Y and Z in each case have the abovementioned meanings.

However, it is also possible to react benzoyl halides of the formula VI

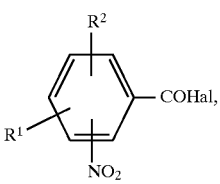

where $R^1$ and $R^2$ in each case have the abovementioned meaning and Hal is chlorine or bromine, with the oxime of a halocarboxamide of the formula VII

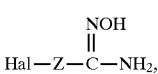

where Hal and Z in each case have the abovementioned meanings, and to allow the resulting oxadiazole of the formula VIII

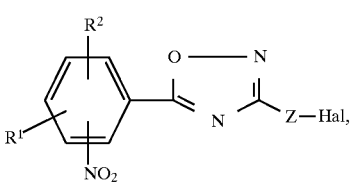

where Hal, $R^1$, $R^2$ and Z in each case have the abovementioned meanings, to react with mercaptoethanol. In this manner a benzene derivative of the formula Id

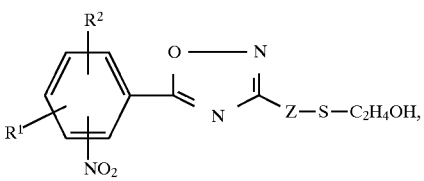

where $R^1$, $R^2$ and Z in each case have the abovementioned meaning, is obtained.

Furthermore, it is also possible to react a benzamide oxime of the formula IX

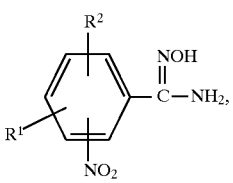

where $R^1$ and $R^2$ in each case have the abovementioned meanings, with a halocarboxylic acid halide of the formula X

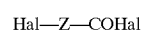

where Hal and Z in each case have the abovementioned meanings, and to react the resulting oxadiazole of the formula XI

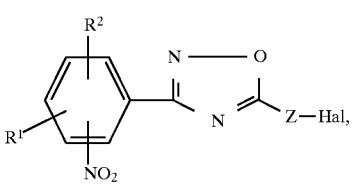

where Hal, $R^1$, $R^2$ and Z in each case have the abovementioned meanings, with mercaptoethanol, a benzene derivative of the formula Ie

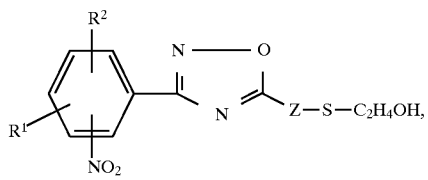

being obtained where $R^1$, $R^2$ and Z in each case have the abovementioned meanings.

If desired, it is then possible, in any desired sequence and in a manner known per se, to reduce the nitro group to the amino group in the benzene derivatives of the formula Id and Ie, to oxidize the sulfur atom to the sulfoxide or sulfonyl group and to convert the 2-hydroxyethyl group into the vinyl group or the group $C_2H_4Q$ where Q is a group which can be removed under alkaline reaction conditions.

In the case of reaction of the nitrile II, it is of course possible to start from those nitriles II which have a thioether group (n=0), a sulfoxide group (n=1) or a sulfonyl group (n=2).

In the case of the nitriles where n=0 and n=1, the oxidation of the sulfur atom, if desired, can then be performed at a later time in the reaction sequence.

This also applies correspondingly to the radical Y in the nitrile II, ie. it is possible to start from starting materials which have a vinyl or 2-hydroxyethyl radical or the radical $C_2H_4Q$ where Q is a group which can be removed under alkaline reaction conditions. The following examples are intended to illustrate the invention in greater detail.

EXAMPLE 1 a. 3-[(2-Hydroxyethylthio)methyl]-5-(3'-nitrophenyl)-1,2,4-oxadiazole

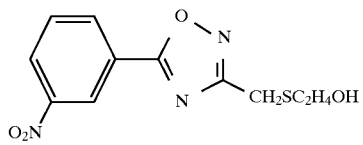

A mixture of 132 g (0.55 mmol) of 3-chloromethyl-5-(3'-nitro-phenyl)-1,2,4-oxadiazole (accessible by reaction of 3-nitrobenzoyl chloride with chloroacetamide oxime), 39.0 ml (0.56 mol) of mercaptoethanol and 80 ml of triethylamine in 700 ml of 1-methoxypropan-2-ol was heated at 100° C. for 4 h and, after cooling, added to ice water. The solid precipitate was filtered off with suction, washed with water and dried at 40° C. under reduced pressure. Yield 142 g (91.8% of theory), slightly yellow powder, m.p. 80° C.

$^1$H-NMR ([$D_6$]DMSO): δ=2.70 (t, 2H, $SCH_2CH_2OH$), 3.60 (br. t, 2H, $CH_2OH$), 3.99 (s, 2H, $SCH_2$-oxadiazole), 4.88 (br. s, 1H, OH), 7.94 (t, 1H, 5'-H), 8.50–8.60 (m, 2H, 4'-H, 6'-H), 8.75 (s, 1H, 2'H).

b. 3-[(2-Hydroxyethylsulfonyl)methyl]-5-(3'-nitrophenyl)-1,2,4-oxadiazole

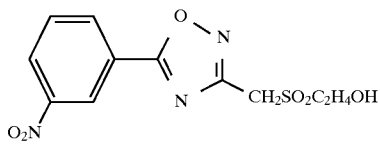

140 g (0.50 mol) of the compound described under a. in 1 l of water were treated with 40 ml of glacial acetic acid, 20 g of sodium acetate and 1 g of sodium tungstate dihydrate and 115 ml (1.13 mol) of 30% strength by weight aqueous hydrogen peroxide solution were then added dropwise at from 70° to 80° C. in the course of 2 h. After addition was complete, the mixture was stirred at 90° C. for a further 2 h. The solid precipitated after cooling was filtered off with suction, washed with water and dried at room temperature under reduced pressure. Yield 105 g (67.0% of theory), slightly yellow powder, m.p. 111° to 113° C.

$^1$H-NMR ([$D_6$]DMSO): δ=3.54 (t, 2H, $SO_2CH_2CH_2OH$), 3.91 (q, 2H, $CH_2OH$), 5.00 (s, 2H, $SO_2CH_2$-oxadiazole), 5.33 (t, 1H, OH), 7.97 (t, 1H, 5'-H), 8.50–8.60 (m, 2H, 4'-H, 6'-H), 8.80 (s, 1H, 2'H).

c. 5-(3'-Aminophenyl)-3-[(2-hydroxyethylsulfonyl)methyl]-1,2,4-oxadiazole

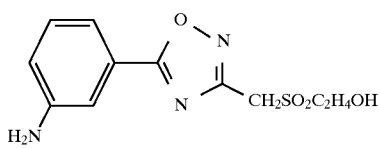

6.10 g (19.5 mmol) of the compound described under b. were introduced into 110 ml (127 mmol) of a 15% strength by weight solution of titanium trichloride in 10% strength by weight hydrochloric acid and the reaction mixture was stirred at room temperature for 20 h. The precipitate which remained was filtered off, the mother liquor was rendered alkaline using sodium hydroxide solution and the precipitate which was deposited was filtered off with suction and dried. The precipitate was then digested with 10 ml of tetrahydrofuran and the insoluble residue was filtered off. The filtrate was evaporated to dryness under reduced pressure and the residue was dried at 50° C. under reduced pressure. Yield 1.40 g (25.3% of theory), ochre powder, m.p. 144° to 145° C.

$^1$H-NMR ([$D_6$]DMSO): δ=3.51 (t, 2H, $SO_2CH_2CH_2OH$), 3.88 (q, 2H, $CH_2OH$), 4.89 (s, 2H, $SO_2CH_2$-oxadiazole), 5.30 (t, 1H, OH), 5.60 (br. s, $_2$H, NH2), 6.86 (d, 1H, 4'-H), 7.22–7.28 (m, 2H, 5'-H, 6'-H), 7.32 (s, 1H, 2'-H).

EXAMPLE 2 a. 3-[2-Hydroxyethylthio)methyl]-5-(4'-nitrophenyl)-1,2,4-oxadiazole

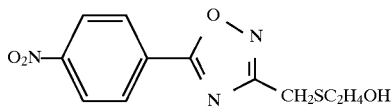

A mixture of 120 g (0.50 mol) of 3-chloromethyl-5-(4'-nitro-phenyl)-1,2,4-oxadiazole (accessible by reaction of 4-nitrobenzoyl chloride with chloroacetamide oxime), 35.0 ml (0.50 mol) of mercaptoethanol and 80 ml of triethylamine in 700 ml of 1-methoxypropan-2-ol was heated at 100° C.

for 4 h and, after cooling, added to ice water. The solid precipitated was filtered off with suction, washed with water and dried at 50° C. under reduced pressure. Yield 131 g (93.1% of theory), slightly yellow crystals.

$^1$H-NMR ([D$_6$]DMSO): δ=2.70 (t, 2H, SC$\underline{H}_2$CH$_2$OH), 3.59 (br. t, 2H, C$\underline{H}_2$OH), 3.98 (s, 2H, SC$\underline{H}_2$-oxadiazole), 4.88 (br. s, 1H, OH), 8.34 (d, 2H, 2'-H, 6'-H), 8.44 (d, 2H, 3'-H, 5'-H).

b. 3-[(2-Hydroxyethylsulfonyl)methyl]-5-(4'-nitrophenyl)-1,2,4-oxadiazole

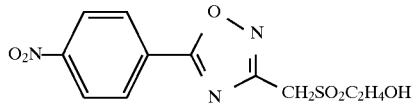

127 g (0.45 mol) of the compound described under a. in 1 l of water were treated with 40 ml of glacial acetic acid, 20 g of sodium acetate and 1 g of sodium tungstate dihydrate and 102 ml (1.00 mol) of 30% strength by weight aqueous hydrogen peroxide were then added dropwise at a temperature of 70 to 80° C. in the course of 2 h. After addition was complete, the mixture was stirred at 90° C. for a further 2 h. The solid precipitated after cooling was filtered off with suction, washed with water and dried at room temperature under reduced pressure. Yield 98.2 g (69.7% of theory), slightly yellow crystals, m.p. 145° C.

$^1$H-NMR ([D$_6$]DMSO): δ=3.53 (t, 2H, SO$_2$C$\underline{H}_2$CH$_2$OH), 3.90 (q, 2H, C$\underline{H}_2$OH), 4.98 (s, 2H, SO$_2$C$\underline{H}_2$-oxadiazole), 5.32 (t, 1H, OH), 8,37 (d, 2H, 2'-H, 6'-H), 8.47 (d, 2H, 3'-H, 5'-H).

c. 5-(4'-Aminophenyl)-3-[(2-hydroxyethylsulfonyl) methyl]-1,2,4-oxadiazole

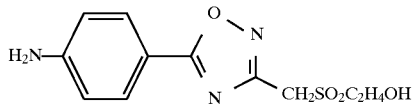

95 g (0.30 mol) of the compound described under b. were dissolved in 1 l of tetrahydrofuran and hydrogenated with addition of 5 g of 10% strength by weight palladium on carbon under normal pressure until hydrogen absorption ceased. The catalyst was filtered off, the solvent was distilled off under reduced pressure and the residue was dried at room temperature under reduced pressure. Yield 80.0 g (95.1% of theory), yellow powder, m.p. 150° to 152 ° C.

$^1$H-NMR ([D$_6$]DMSO): δ=3.53 (t, 2H, SO$_2$C$\underline{H}_2$CH$_2$OH), 3.90 (br. t, 2H, C$\underline{H}_2$OH), 4.84 (s, 2H, SO$_2$C$\underline{H}_2$-oxadiazole), 5.30 (br. s, 1H, OH), 6.95 (d, 2H, 3'-H, 5'-H), 7.91 (d, 2H, 2'-H, 6'-H).

EXAMPLE 3 a. 3-(2-Hydroxyethylsulfonyl)propionitrile

328 g (2.50 mol) of 3-[(2-Hydroxyethyl)thio]propionitrile in 500 ml of water were treated with 10 ml of glacial acetic acid, 2 g of sodium acetate and 2 g of sodium tungstate dihydrate and 520 ml (5.09 mol) of 30% strength by weight aqueous hydrogen peroxide were then added dropwise at from 60 to 70° C. in the course of 4 h. In order to maintain the given temperature range, the reaction mixture had to be cooled with ice water from time to time. After cooling, excess hydrogen peroxide was destroyed with sodium dithionite and the solvent was distilled off under reduced pressure. The oily residue was digested with 200 ml of acetone and the precipitate was filtered off. The filtrate was concentrated to dryness under reduced pressure. 405 g of a viscous oil having a content of pure 3-(2-hydroxyethylsulfonyl)propionitrile of 86.4% (85.8% of theory) were obtained.

$^1$H-NMR ([D$_6$]DMSO): δ=2.98 (t, 2H, C$\underline{H}_2$CN), 3.32 (t, 2H, SO$_2$C$\underline{H}_2$CH$_2$OH), 3.49 (t, 2H, SO$_2$C$\underline{H}_2$CH$_2$CN), 3.78 (br. t, 2H, C$\underline{H}_2$OH), 5.22 (br. s, 1H, OH).

(see also EP-A 639 562).

b. 3-(2-Hydroxyethylsulfonyl)propionamide oxime

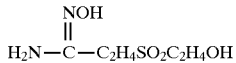

190 ml (1.00 mol) of a 30% strength by weight solution of sodium methoxide in methanol were added dropwise to a solution of 163 g (1.00 mol) of the compound described under a. and 69.5 g (1.00 mol) of hydroxylammonium chloride in 1 l of methanol. The reaction mixture was heated to boiling under reflux for 6 h. After cooling, the precipitate was filtered off with suction and dried at 50° C. under reduced pressure. 151 g of a pale brown microcrystalline powder having a content of 3-(2-hydroxyethylsulfonyl) propionamide oxime of 71.4% were obtained (55.0% of theory).

$^1$H-NMR ([D$_6$]DMSO): δ=2.45 (t, 2H, C$\underline{H}_2$C(NH$_2$)=NOH), 3.22–3.38 (m, 4H, C$\underline{H}_2$SO$_2$C$\underline{H}_2$), 3.80 (br. t, 2H, CH$_2$OH), 5.26 (br. s, 1H, CH$_2$O$\underline{H}$), 5.56 (br. s, 2H, NH$_2$), 9.02 (br. s, 1H, N—OH).

c. 5-(2'-Aminophenyl)-3-[2-(2-hydroxyethylsulfonyl) ethyl]-1,2,4-oxadiazole

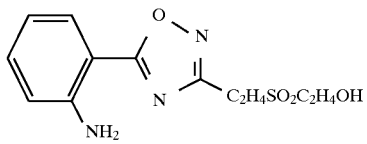

81.6 g (0.50 mol) of isatoic anhydride were slowly introduced into a solution, warmed to 50° C., of 98.1 g (0.50 mol) of the compound described under b. in 1 l of 1-methoxypropan-2-ol and the reaction mixture was heated to boiling under reflux for 6 h after completion of the evolution of gas. The solvent was then distilled off under reduced pressure, the residue which remained was covered with isopropanol and the precipitate which was deposited was filtered off with suction. Yield 76.8 g (51.7% of theory), beige powder, m.p. 118° to 119° C.

$^1$H-NMR ([D$_6$]DMSO): δ=3.25 (t, 2H, C$\underline{H}_2$-oxadiazole), 3.35 (t, 2H, SO$_2$C$\underline{H}_2$CH$_2$OH), 3.63 (t, 2H, SO$_2$C$\underline{H}_2$CH$_2$-oxadiazole), 3.77 (q. 2H, C$\underline{H}_2$OH), 5.19 (t, 1H, O$\underline{H}$), 6.65 (t, 1H, 5'-H), 6.87 (br. s, 2H, NH$_2$), 6.90 (d, 1H, 3'-H), 7.30 (t, 1H, 4'-H), 7.76 (d, 1H, 6'-H).

MS (ET): m/z (M$^+$)=297.

EXAMPLE 4 a. 5-(Chloromethyl)-3-(4'-chloro-3'-nitrophenyl)-1,2,4-oxadiazole

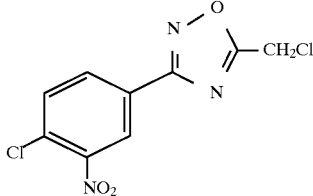

127 ml (1.60 mol) of chloroacetyl chloride were added dropwise to a solution of 323 g (1.50 mol) of 4-chloro-3-nitrobenzamide oxime and 130 ml (1.61 mol) of pyridine in 2 l of dioxane. The reaction mixture was then refluxed for 4 h and, after cooling, stirred into 3 l of ice water. The precipitate was filtered off with suction, washed with water and dried at room temperature under reduced pressure. Yield 300 g (73.0% of theory), slightly yellow powder, m.p. 55 to 56° C.

$^1$H-NMR ([D$_6$]DMSO): δ=5.23 (s, 2H, C$\underline{H}_2$Cl), 8.00 (d, 1H, 5'-H), 8.28 (d, 1H, 6'-H), 8.61 (s, 1H, 2'-H).

b. 5-[(2-Hydroxyethylthio)methyl]-3-[4'-(2-hydroxyethylthio)-3'-nitrophenyl]-1,2,4-oxadiazole

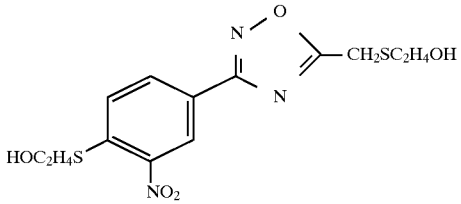

105 ml (1.50 mol) of mercaptoethanol were added dropwise to a solution of 164 g (0.60 mol) of the compound described under a. and 210 ml of triethylamine in 1 l of 1-methoxypropan-2-ol. The reaction mixture was then refluxed for 6 h and, after cooling, introduced into 1.5 l of ice water. The precipitate was filtered off with suction, washed with water and dried at room temperature under reduced pressure. Yield 170 g (79.3% of theory), yellow powder, m.p. 106° to 107° C.

$^1$H-NMR ([D$_6$]DMSO): δ=2.77 (t, 2H, CH$_2$SC$\underline{H}_2$CH$_2$OH), 3.25 (t, 2H, aryl-SCH$_2$C$\underline{H}_2$OH), 3.61 (q, 2H, CH$_2$SCH$_2$C$\underline{H}_2$OH), 3.73 (q, 2H, aryl-SCH$_2$C$\underline{H}_2$OH), 4.24 (s, 2H, oxadiazole-C$\underline{H}_2$S), 4.91 (t, 1H, CH$_2$SCH$_2$CH$_2$O$\underline{H}$), 5.15 (t, 1H, aryl-SCH$_2$CH$_2$O$\underline{H}$), 7.87 (d, 1H, 5'-H), 8.21 (d, 1H, 6'-H), 8.67 (s, 1H, 2'-H).

c. 5-[(2-Hydroxyethylsulfonyl)methyl]-3-[4'-(2-hydroxyethyl-sulfonyl)-3'-nitrophenyl]-1,2,4-oxadiazole

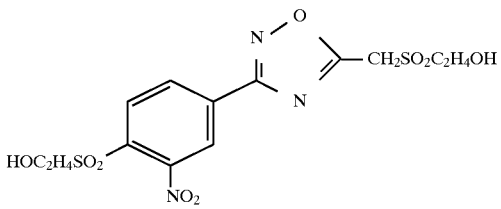

143 g (0.40 mol) of the compound described under b. in 1 l of water were treated with 30 ml of glacial acetic acid, 20 g of sodium acetate and 2 g of sodium tungstate dihydrate and 150 ml (1.47 mol) of 30% strength by weight aqueous hydrogen peroxide were added dropwise at 80° C. in the course of 2 h. The mixture was then refluxed, a further 150 ml (1.47 mol) of 30% strength by weight aqueous hydrogen peroxide were added dropwise in the course of 2 h and the mixture was subsequently stirred under reflux for 3 h. The solid precipitated after cooling was filtered off with suction, washed with a little cold water and dried at 50° C. under reduced pressure. Yield 104 g (61.7% of theory), slightly yellow crystals, m.p. 126° C.

$^1$H-NMR ([D$_6$]DMSO): δ=3.58 (t, 2H, CH$_2$SO$_2$C$\underline{H}_2$CH$_2$OH), 3.79–3.92 (m, 6H, aryl-SO$_2$C$\underline{H}_2$CH$_2$OH, CH$_2$SO$_2$CH$_2$C$\underline{H}_2$OH, aryl-SO$_2$—CH$_2$C$\underline{H}_2$OH), 5.06 (br. s, 1H, aryl-SO$_2$CH$_2$CH$_2$O$\underline{H}$), 5.31 (s, 2H, oxadiazole-C$\underline{H}_2$SO$_2$), 5.37 (br. s, 1H, CH$_2$SO$_2$CH$_2$CH$_2$O$\underline{H}$), 8.31 (d, 1H, 5'-H), 8.53 (d, 1H, 6'-H), 8.63 (s, 1H, 2'-H).

d. 3-[3'-Amino-4'-(2-hydroxyethylsulfonyl)phenyl]-5-[(2-hydroxy-ethylsulfonyl)methyl]-1,2,4-oxadiazole

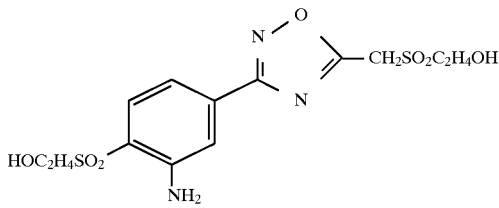

105 g (0.25 mol) of the compound described under c. were introduced into 1.4 l (1.62 mol) of a 15% strength by weight solution of titanium trichloride in 10% strength by weight hydrochloric acid and the reaction mixture was stirred at room temperature for 20 h. The precipitate was filtered off with a little water and dried. Yield 90.3 g as hydrochloride (84.4% of theory), pale brown crystals, m.p. 157° C. (dec.).

In order to obtain the free base, the product was suspended in water and neutralized with aqueous ammonia solution. The precipitate was filtered off with suction and recrystallized from methanol.

Analysis: calc. C 39.9 H 4.4 N 10.7 O 28.6 S 16.4
found C 39.7 H 4.4 N 10.7 O 28.2 S 16.4
MS (ESI): m/z (M$^+$H$^+$)=392.

$^1$H-NMR ([D$_6$]DMSO): δ=3.44 (t, 2H, aryl-SO$_2$C$\underline{H}_2$CH$_2$OH), 3.58 (t, 2H, CH$_2$SO$_2$C$\underline{H}_2$CH$_2$OH), 3.69 (q, 2H, aryl-SO$_2$CH$_2$C$\underline{H}_2$OH). 3.88 (q, 2H, CH$_2$SO$_2$CH$_2$C$\underline{H}_2$OH), 4.89 (t, 1H, aryl-SO$_2$CH$_2$CH$_2$O$\underline{H}$), 5.26 (s, 2H, oxadiazole-C$\underline{H}_2$SO$_2$), 5.35 (t, 1H, CH$_2$SO$_2$CH$_2$CH$_2$O$\underline{H}$), 6.39 (br. s, 2H, NH$_2$), 7.27 (d, 1H, 6'-H), 7.61 (s, 1H, 2'-H), 7.66 (d, 1H, 5'-H).

EXAMPLE 5 a. 3-(2-Hydroxyethylthio)propionamide oxime

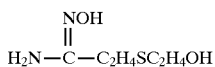

190 ml (1.00 mol) of a 30% strength by weight solution of sodium methoxide in methanol were added dropwise to a solution of 131 g (1.00 mol) of 3-(2-hydroxyethylthio)propionitrile and 69.5 g (1.00 mol) of hydroxylammonium chloride in 1 l of methanol. The reaction mixture was refluxed for 6 h. After cooling, the precipitate was filtered off with suction and the filtrate was evaporated to dryness under reduced pressure. 152 g of a viscous oil having a content of pure 3-(2-hydroxyethylthio)propionamide oxime of 82.4% were obtained (76.3% of theory).

$^1$H-NMR ([D$_6$]DMSO): δ=2.20 (t, 2H, C$\underline{H}_2$C(NH$_2$)=NOH), 2.57 (t, 2H, SO$_2$C$\underline{H}_2$), 2.68 (t, 2H, SO$_2$C$\underline{H}_2$), 3.52 (br. t, 2H, C$\underline{H}_2$OH), 4.79 (br. s, 1H, CH$_2$O$\underline{H}$), 5.40 (br. s, 2H, NH$_2$), 8.81 (br. s, 1H, N—OH).

b. 5-(2'-Aminophenyl)-3-[2-(2-hydroxyethylthio)ethyl]-1,2,4-oxadiazole

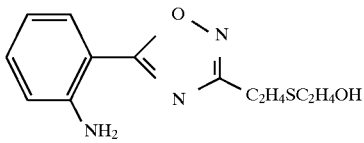

81.6 g (0.50 mol) of isatoic anhydride were slowly introduced into a solution, which was warmed to 50° C., of 82.1 g (0.50 mol) of the compound described under a. in 1 l of 1-methoxypropan-2-ol and the reaction mixture was refluxed for 6 h after evolution of gas was complete. The solvent was then distilled off under reduced pressure and the residue was covered with a layer of isopropanol. The precipitate was filtered off with suction and dried. Yield 80.9 g (61.0% of theory of beige powder.
$^1$H-NMR ([D$_6$] DMSO): δ=2.95 (t, 2H, CH$_2$-oxadiazole), 2.70 (t, 2H, SO$_2$CH$_2$CH$_2$OH), 3.01 (t, 2H, SO$_2$CH$_2$CH$_2$-oxadiazole, 3.47 (q, 2H, CH$_2$OH), 4.74 (t, 1H, OH), 6.62 (t, 1H, 5'-H), 6.85 (br.s., 2H, NH$_2$), 6.92 (d, 1H, 3'-H), 7.22 (t, 1H, 4'-H), 7.71 (d, 1H, 6'-H).

c. 5-(2'-Aminophenyl)-3-[2-(2-hydroxyethylsulfonyl)ethyl]-1,2,4-oxadiazole

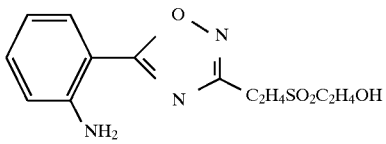

79.7 g (0.30 mol) of the compound described under b. in 150 ml of 30% strength sulfuric acid were treated with 0.5 g of sodium tungstate dihydrate. 65 ml (0.64 mol) of 30% strength by weight aqueous hydrogen peroxide were then added dropwise at from 60° to 70° C. in the course of 2 h. After cooling, the reaction mixture was added to 500 g of ice and rendered neutral with dilute sodium hydroxide solution. The precipitate was filtered off with suction and washed three times with 80 ml of methanol each time. Yield 72.8 g (81.6% of theory), beige powder, m.p. 118° to 120° C.
$^1$H-NMR ([D$_6$]DMSO): δ=3.25 (t, 2H, CH$_2$-oxadiazole), 3.35 (t, 2H, SO$_2$CH$_2$CH$_2$OH), 3.63 (t, 2H, SO$_2$CH$_2$CH$_2$-oxadiazole), 3.77 (q, 2H, CH$_2$OH), 5.19 (t, 1H, OH), 6.65 (t, 1H, 5'-H), 6.87 (br. s, 2H, NH$_2$), 6.90 (d, 1H, 3'-H), 7.30 (t, 1H, 4'-H), 7.76 (d, 1H, 6'-H).
MS (EI): m/z (M$^+$)=297.

EXAMPLE 6 a. 3-(4'-Chloro-3'-nitrophenyl)-5-vinyl-1,2,4-oxadiazole

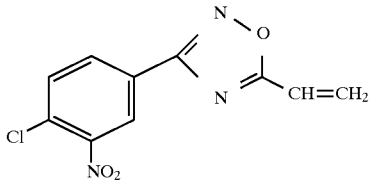

58 ml (0.71 mol) of acryloyl chloride were added dropwise to a solution of 151 g (0.70 mol) of 4-chloro-3-nitrobenzamide oxime and 60 ml (0.74 mol) of pyridine in 1.5 l of dioxane and the reaction mixture was then refluxed for 12 h. After cooling, the dioxane phase was decanted off from insoluble constituents, the solvent was distilled off under reduced pressure and the residue was stirred into 1.5 l of ice water. The precipitated solid was filtered off with suction, washed with water, recrystallized from methanol and dried under reduced pressure at room temperature. Yield 130 g (74.0% of theory), slightly yellow powder, m.p. 86°–88° C.
$^1$H-NMR ([D$_6$]DMSO): δ=6.24 (d, 1H, cis-CH=CH$_2$), 6.66 (d, 1H, trans-CH=CH$_2$), 7.02 (dd, 1H, CH=CH$_2$), 8.03 (d, 1H, 5'-H), 8.32 (d, 1H, 6'-H), 8.64 (s, 1H, 2'-H).

b. 5-[(2-Hydroxyethylmercapto)ethyl]-3-[4'-(2-hydroxyethylmercapto)-3'-nitrophenyl]-1,2,4-oxadiazole

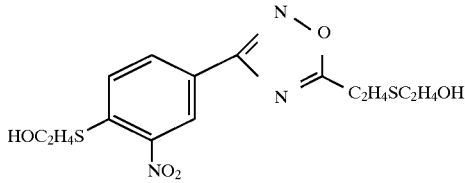

35 ml (0.50 mol) of mercaptoethanol were added dropwise to a solution of 126 g (0.50 mol) of the 3-(4'-chloro-3'-nitro-phenyl)-5-vinyl-1,2,4-oxadiazole prepared under a. and 5 ml (0.05 mol) of piperidine in 800 ml of 1-methoxypropan-2-ol and the reaction mixture was stirred at 50° C. for 6 h. A further 35 ml (0.50 mol) of mercaptoethanol and 70 ml (0.50 mol) of triethylamine were then added dropwise and the reaction mixture was refluxed for 10 h. After cooling, the solvent was distilled off under reduced pressure and the residue was stirred into 1 l of ice water. The precipitated solid was filtered off with suction, washed with water and methanol and dried under reduced pressure at room temperature. Yield 153 g (82.4% of theory, yellow powder, m.p. 85°–88° C.
$^1$H-NMR ([D$_6$]DMSO): d=2.67 (t, 2H, CH$_2$CH$_2$SCH$_2$CH$_2$OH), 3.06 (t, 2H, CH$_2$CH$_2$SCH$_2$CH$_2$OH), 3.24 (t, 2H, aryl-SCH$_2$CH$_2$OH), 3.35 (t, 2H, CH$_2$CH$_2$SCH$_2$CH$_2$OH), 3.59 (br. t, 2H, CH$_2$CH$_2$SCH$_2$CH$_2$OH), 3.74 (br. t, 2H, aryl-SCH$_2$CH$_2$OH), 4.87 (br. s, 1H, CH$_2$SCH$_2$CH$_2$OH), 5.16 (br. s, 1H, Aryl-SCH$_2$CH$_2$OH), 7.84 (d, 1H, 5'-H), 8.18 (d, 1H, 6'-H), 8.64 (s, 1H, 2'-H).

c. 5-[(2-Hydroxyethylsulfonyl)ethyl]-3-[4'-(2-hydroxyethylsulfonyl)-3'-nitrophenyl]-1,2,4-oxadiazole

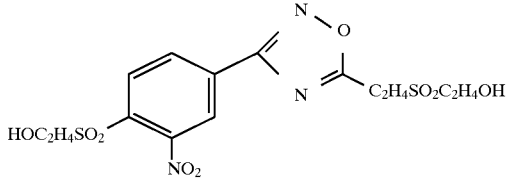

149 g (0.40 mol) of the 5-[(2-hydroxyethylmercapto)ethyl]-3-[4'-(2-hydroxyethylmercapto)-3'-nitrophenyl]-1,2,4-oxadiazole prepared under b. in 1 l of water were treated with 50 ml of glacial acetic acid, 20 g of sodium acetate and 2 g of sodium tungstate dihydrate. 130 ml (1.27 mol) of a 30% strength by weight aqueous hydrogen peroxide solution were added dropwise at 80° C. in the course of 2 h. The mixture was then refluxed, a further 130 ml (1.27 mol) of a 30% strength by weight aqueous hydrogen peroxide solution were added dropwise in the course of 2 h and the mixture was refluxed for 3 h. The solid precipitated after cooling was filtered off with suction, washed with water, recrystallized from n-butanol and dried under reduced pressure at 50° C. Yield 126 g (72.3% of theory, slightly yellow crystals, m.p. 140°–142° C.

1H-NMR ([$D_6$]DMSO): δ=3.38 (t, 2H, $CH_2CH_2SO_2CH_2CH_2OH$), 3.57 (t, 2H, $CH_2CH_2SO_2CH_2CH_2OH$), 3.77 (t, 2H, $CH_2CH_2SO_2CH_2CH_2OH$), 3.81–3.87 (m, 6H, aryl-$SO_2CH_2CH_2OH$, $CH_2CH_2SO_2CH_2CH_2OH$, aryl-$SO_2CH_2CH_2OH$), 5.05 (br.s, 1H, aryl-$SO_2CH_2CH_2OH$), 5.25 (br.s, 1H, $CH_2CH_2SO_2CH_2CH_2OH$), 8.30 (d, 1H, 5'-H), 8.50 (d, 1H, 6'-H), 8.59 (s, 1H, 2'-H).

d. 3-[3'-Amino-4'-(2-hydroxyethylsulfonyl)phenyl]-5-[(hydroxyethylsulfonyl)ethyl]-1,2,4-oxadiazole

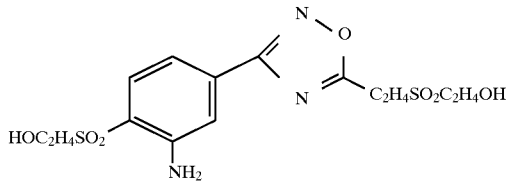

43.5 g (0.10 mol) of 5-[(2-hydroxyethylsulfonyl)ethyl]-3-[4'-(2-hydroxyethylsulfonyl)-3,-nitrophenyl]-1,2,4-oxadiazole (prepared under c.) in 300 ml of 1-methoxypropan-2-ol were warmed to 60° C., 800 ml of water were added and, in the course of 3 h, a total of 25 g of iron meal were introduced. During the course of this, the pH was kept at from 3.5 to 4.0 by addition of glacial acetic acid. After cooling, the reaction mixture was filtered and the solvent was distilled off from the mother liquor under reduced pressure. The residue which remained was stirred with methanol, and the precipitated solid was filtered off with suction, recrystallized from n-butanol and dried under reduced pressure at 50° C. Yield 22 g (54.3% of theory), pale brown powder, m.p. 208°–210° C. (dec.).
MS (ESI): m/z ([M−H]$^+$)=404, ([M+CI]$^+$)=440.

We claim:

1. A benzene derivative of formula I

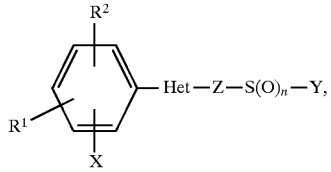

wherein n is 0, 1 or 2;

X is nitro or amino;

Z is a direct bond or $C_{1-6}$-alkylene, optionally interrupted by 1 or 2 oxygen or sulfur atoms as ether functional groups, or 1 or 2 non-adjacent imino, $C_{1-4}$-alkylamino or $C_{1-4}$-alkanoylimino groups;

Y is vinyl or a group of the formula $C_2H_4$—Q, wherein Q is hydroxyl or a group which can be removed under alkaline reaction conditions;

$R^1$ and $R^2$ independently of each other, are each hydrogen, $C_{1-4}$-alkyl, $C_{1-4}$-alkoxy, halogen, nitro, amino, hydroxysulfonyl or a group of the formula Z—S(O)$_n$—Y, where n, Z and Y each have the above stated meanings; and Het is a divalent bridging moiety selected from the group consisting of 1,2,4-oxadiazole-3,5-diyl, 1,3,4-oxadiazole-2,5-diyl, 1,2,4-thiadiazole-3,5-diyl or 1,3,4-thiadiazole-2,5-diyl.

2. The benzene derivative as claimed in claim 1, wherein n is 0 or 2.

3. The benzene derivative as claimed in claim 1, wherein Z is $C_{1-4}$-alkylene.

4. The benzene derivative as claimed in claim 3, wherein $C_{1-4}$-alkylene is interrupted by an oxygen atom in the form of an ether group.

5. The benzene derivative as claimed in claim 1, wherein Y is 2-hydroxyethyl.

6. The benzene derivative as claimed in claim 1, wherein $R^1$ has the meanings defined in claim 1 and $R^2$ is hydrogen.

7. The benzene derivative as claimed in claim 1, wherein Het is 1,2,4-oxadiazole-3,5-diyl.

8. The benzene derivative as claimed in claim 1, wherein $R^1$ is hydrogen, nitro, amino, hydroxysulfonyl or a radical of the formula S(O)$_n$C$_2$H$_4$OH, where n is 0 or 2, and $R^2$ is hydrogen.

9. The benzene derivative as claimed in claim 1, which has formula Ia or Ib

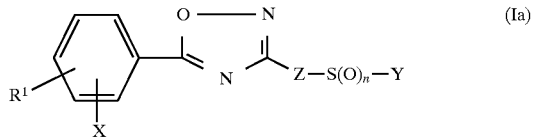

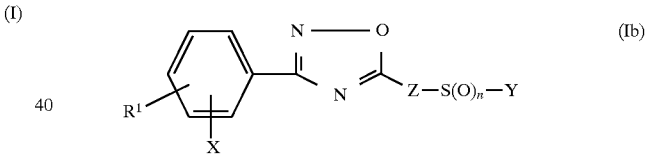

wherein n is 0 or 2,

X is nitro or amino,

Z is $C_1$–$C_4$-alkylene and $R^1$ is hydrogen, nitro, amino, hydroxysulfonyl or a radical of the formula S(O)$_n$C$_2$H$_4$OH, where n is 0 or 2, and Y has the meaning mentioned in claim 1.

* * * * *